US006482429B1

(12) United States Patent
Etzler

(10) Patent No.: US 6,482,429 B1
(45) Date of Patent: Nov. 19, 2002

(54) STABLE POWDER INHALATION DOSAGE FORMULATION

(75) Inventor: Frank M. Etzler, New Milford, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/885,349

(22) Filed: Jun. 20, 2001

(51) Int. Cl.[7] .......................... A61K 9/68; A61B 5/055; B32B 15/02

(52) U.S. Cl. .................... 424/440; 424/9.35; 428/402.2

(58) Field of Search ................................ 424/440, 9.35; 428/402.2

(56) References Cited

U.S. PATENT DOCUMENTS 5,679,459 A * 10/1997 Riess et al. .............. 428/402.2
5,738,865 A * 4/1998 Baichwal et al. ........... 424/440

* cited by examiner

*Primary Examiner*—Jose'G. Dees
*Assistant Examiner*—Robert M DeWitty
(74) *Attorney, Agent, or Firm*—Rober P. Raymond; Mary-Ellen M. Devlin; Alan R. Stempel

(57) ABSTRACT

An insufflation for the administration of a drug into a body cavity is described where the carrier for the drug is a finely divided powder selected from the group consisting of myoinositol, mannitol and cellobiose.

7 Claims, 2 Drawing Sheets

STABLE POWDER INHALATION DOSAGE FORMULATION

BACKGROUND OF THE INVENTION

The present invention relates to a powder pharmaceutical formulation, which may be used as a carrier vehicle for the administration of drugs. The powder pharmaceutical formulation of the present invention is particularly adapted for administration as an insufflation into a body cavity. Specifically, such formulation can be used in dry powder inhalers for pulmonary delivery. Examples of drugs for pulmonary delivery are albuterol sulfate, ipratropium bromide and tiotropium bromide. However, other drugs may be incorporated into the formulation of the present invention.

Capsules are frequently used as a storage means for finely divided, pharmaceutical powders comprising active drug that is to be delivered to a patient via inhalation. For example, to avoid the use of propellant gases, some of which (chloro-fluoro-carbons or CFCs) have been implicated in environmental damage (depletion of the ozone layer in the atmosphere), dry powder comprising an active drug constituent is placed into a capsule. The capsule is loaded into a dry powder inhaler (DPI), the inhaler is used to administer the drug product. Generally, such devices cut or pierce the capsules comprising the dry powder prior to administration, and the powder is then inhaled by the patient.

The capsules usually consist of two (2) halves that are usually supplied by the capsule manufacturer in an assembled (closed) but not locked state. During capsule filling, the two halves are separated, filled with the pharmaceutical powder formulation comprising the active drug, and then closed and locked for insertion into the DPI. Often, the capsule is a hard, gelatin capsule. Hard cellulose and plastic capsules suitable for storing pharmaceutical powders are also used. Such capsules are available from Capsugel (Belgium), Su-Heung (South Korea) and Elamco (United States), among other manufacturers.

Where the active drug in the powdered pharmaceutical formulation is to be delivered to the upper, respiratory tract (i.e., intranasally), the particles of active drug should be about 20 to about 100 micrometers in size. Where administration of the active drug is to be to the lower respiratory tract (i.e., intrapulmonary), the particles of active drug are preferably less than about 5 micrometers in size.

Such small sizes present handling problems (i.e., filling the capsules during manufacture), so the active drug is usually mixed with a coarse carrier. The carrier is typically a soluble hexose such as glucose or lactose, or mannitol. The carrier also functions as a bulking agent for an active drug having a low dose regimen. See, for example, U.S. Pat. No. 5,254,335. Additionally, many drugs used in inhalation therapy are given in small doses regardless, i.e., less than about 250 micrograms, and so bulking agents are routinely used.

Ipratropium bromide is an active drug that is typically administered via inhalation. It presents problems for use in DPIs since the amount of ipratropium bromide to be administered is very low (<50 micrograms). Accordingly, ipratropium bromide must be blended with a bulking agent, such as lactose or glucose, for administration via DPIs.

The soluble hexoses used as carriers for inhalable drugs are non-toxic and tend to be stable in the presence of active drug substance. However, the soluble hexoses tend to be hygroscopic and require special packaging to prevent moisture from contacting the powdered formulation, and thereby causing the formulation to become unusable due to caking and lump formation.

BRIEF SUMMARY OF THE INVENTION

The applicant has discovered that certain non-toxic and pharmaceutically acceptable powdered materials have reduced sensitivity to moisture, but also have the requisite biocompatibility that permits the use of these non-toxic, pharmaceutically acceptable powdered materials as a vehicle for the formulation of an insufflation.

The invention provides an insufflation for the administration of a drug into a body cavity. The dosage form comprises an effective amount of a drug, which is active when administered as an insufflation, and a carrier powder which is a finely divided powder selected from the group consisting of myo-inositol, mannitol and cellobiose. The invention also includes a method of administering a drug as an insufflation which comprises administering into a body cavity an effective amount of a drug dispersed in a finely divided powder selected from the group consisting of myo-inositol, mannitol, cellobiose and mixtures thereof.

Accordingly, it is a primary object of the invention to provide a novel drug powder formulation, which may be administered as an insufflation.

It is also an object of the invention to provide a stable, free-flowing composition of a drug, which will resist the effect of moisture and high humidity, can be dispensed as an insufflation.

It is also an object of the invention to provide a method for the administration of a drug in a powder formulation, which permits administration of the drug as an insufflation.

These other objects of the invention will become apparent from the specification hereinafter presented.

DETAILED DESCRIPTION OF THE INVENTION

Figure 1:
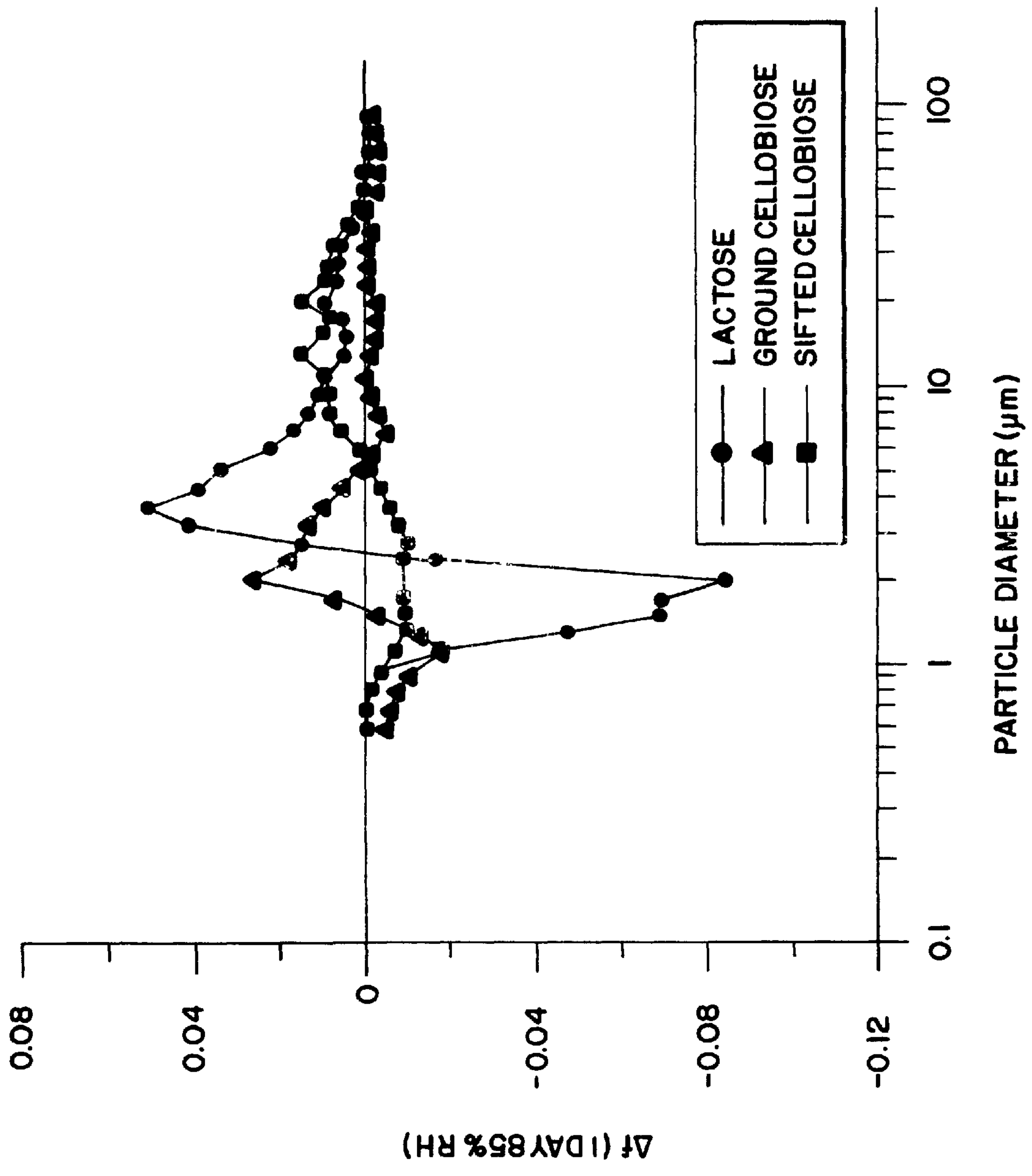
FIG. 1 is a graph of the relative sintering rates of sifted cellobiose, ground celloboise and lactose under conditions of 85% relative humidity.

The performance of powder, inhalation capsules is affected by a number of factors. Among such factors, exposure to high (>60% RH) humidity is known to reduce respirable mass. Cellobiose is an alternative to lactose in formulations of pharmaceutical powders for inhalation due to its lower sintering rate in high humidity. Cellobiose is a disaccharide with a structure very similar to that of lactose.

In the following work, a formulation containing cellobiose was compared to a formulation containing lactose using particle sizing and capsule retention measurements. The particle size distributions of cellobiose, lactose, a lactose/ipratropium bromide blend and a cellobiose/ipratropium bromide blend were measured using the Aerosizer (Amherst Processing Instruments). The particle size distributions of blends of cellobiose or lactose with ipratropium bromide were measured using the Aerobreather product manufactured by Amherst Processing Instruments, a device used to measure the particle size distribution of inhaled particles. Capsule retention of cellobiose or lactose blends with ipratropium bromide was determined manually by measuring the powder retained within the capsule after dumping powder out. These experiments are intended to compare some of the performance characteristics of the two formulations under normal, low humidity (<60% RH) conditions.

A sample of cellobiose lot 62H0042 (Sigma Chemical Company) was milled with a mortar and pestle and sifted with a 200 mesh screen using the Sonic Sifter UP by ATM (Serial #A3075). The cellobiose that passed through the screen was collected for experimental use. A blend of 190 mg of cellobiose and 10 mg of ipratropium bromide was made. A blend of 190 mg of lactose (Pharmatose 200M) and 10 mg of ipratropium bromide was also made. The ipratropium bromide was supplied by Boehringer Ingelheim Pharmaceuticals, Inc., of Ridgefield, Conn. Pharmatose 200 M is the commercial name for a sized product comprising lactose monohydrate.

The particle size distribution of the milled cellobiose, Pharmatose 200M and the cellobiose/ipratropium bromide blend was measured using the Aerosizer (Serial #50961117). The Pulse Jet Disperser device (Amherst Processing Instruments) was used for powder dispersion. Three measurements were made for each sample and the results were averaged. Particle size distribution measurements of a lactose(Pharmatose 200 M)/ipratropium bromide blend were used to compare with the cellobiose/ipratropium bromide blend.

Su Heung capsules were filled with 5.5 mg of the cellobiose and Pharmatose 200M blends and then locked. Particle size distributions of the inhaled particles from each blend were measured using the Aerobreather (Serial #0269904A), an instrument that attaches to the Aerosizer and simulates inhalation at different flowrates. In order to measure the particle size distribution of the inhaled particles, the capsules were placed in the a dry powder inhaler and the inhaler was placed into the mouthpiece of the Aerobreather. Each capsule was then pierced prior to inhalation by the Aerobreather. The particle size distributions of the inhaled particles were measured at three different inhalation rates: 20, 40, and 60 l/min. At each flowrate, the particle size distributions of the inhaled particles were measured in triplicate and then averaged.

Capsule retention of the cellobiose/ipratropium bromide blend and lactose/ipratropium bromide blend was measured using capsule lots 72602 (Su Heung), 27985 (Capsugel), supercritical fluid extracted 29625(Capsugel) [see U.S. Pat. No. 6,228,394, issued May 8, 2001], and 31810P(Capsugel). About 5.5 mg +/−0.5 mg of the powder blend was placed into each capsule. The capsule was closed and shaken to disperse the powder throughout the capsule. The capsule was then opened and the blend dumped out of the capsule. The amount of powder remaining in the capsule was then measured gravimetrically. This procedure was repeated ten times for each sample. The results of the ten determinations were averaged.

Table 3:1 below shows the particle size distributions and mean particle sizes of the milled cellobiose, lactose, a cellobiose/ipratropium bromide blend and a lactose/ipratropium bromide blend as measured using the Aerosizer and Pulse Jet Disperser.

TABLE 3:1

Mean Particle Size of Lactose, Cellobiose and Ipratropium Bromide Blends as Measured Using an Aerosizer

| | Mean Particle Size (μm) | Standard Deviation of Three Means |
|---|---|---|
| Lactose | 2.044 | 0.204 |
| Cellobiose | 2.032 | 0.142 |
| Cellobiose/IB | 2.826 | 0.032 |
| Lactose/IB | 2.309 | 0.019 |

The mean particle sizes of the cellobiose and lactose samples were almost identical, while the mean particle size of each blend was higher than that of the unblended sugar. The cellobiose sample has more particles under 2 gm and above 10 gm than did the lactose sample. The cellobiose/ipratropium bromide blend has fewer particles under 10 gm and more above 10 gm than did the cellobiose sample. The larger particle sizes for each of the blends indicate that the sugar particles are adhering to ipratropium particles to create larger composite particles. The cellobiose/ipratropium bromide blend has a higher mean particle size than the lactose/ipratropium bromide blend. This result may indicate that cellobiose has somewhat stronger adhesion to ipratropium bromide than does lactose, or alternatively, may reflect differences in the respective particle size distributions of the constituent components.

TABLE 3:2 below shows the particle size distributions and mean particle size of blends of ipratropium bromide and lactose or cellobiose, which were inhaled into the Aerobreather at 20, 40 and 60 l/min.

TABLE 3:2

Mean Particle Size of Blends of Ipratropium Bromide and Lactose or Cellobiose Extracted from Capsules Using and Aerobreather

| | Breath Rate (l/min) | Mean Particle Size (μm) | Standard Deviation of Three Means |
|---|---|---|---|
| Lactose/Ipratropium | 20 | 1.875 | 0.037 |
| Bromide | 40 | 1.601 | 0.011 |
| | 60 | 1.562 | 0.022 |
| Cellobiose/ | 20 | 1.655 | 0.038 |
| Ipratropium | 40 | 1.402 | 0.019 |
| Bromide | 60 | 1.382 | 0.041 |

The cellobiose blend has a lower mean particle size than the lactose blend at all three inhalation rates, which is the opposite of the particle sizing results from the Aerosizer. The peaks of the distributions for the cellobiose blend are shifted to lower particle sizes than the lactose blend at all inhalation rates. The difference could reflect differences in adhesion strength, particle size distribution or size selection of retained particles.

TABLE 3:3 below shows the retention of ipratropium bromide and cellobiose or lactose blends after manual retention tests.

TABLE 3:3

Retention of Lactose/Ipratropium Bromide Blend and a Cellbiose/Ipratropium Bromide Blend in Capsules

| Powder Blend | Capsule Lot | Retention (%) | Standard Deviation |
|---|---|---|---|
| Lactose/IB | 72602 | 3.36 | 2.07 |
| | 27985 | 7.18 | 1.70 |
| | 29625SFE | 5.09 | 2.92 |
| | 31810P | 9.19 | 2.63 |
| Cellobiose/IB | 72602 | 5.10 | 2.86 |
| | 27985 | 11.35 | 2.69 |
| | 29625SFE | 8.30 | 5.11 |
| | 31810P | 12.76 | 6.58 |

The retention tests show that lactose has slightly lower retention than cellobiose. This occurs independent of capsule type used. It is likely that cellobiose adheres somewhat more strongly to the capsule surface than does lactose.

In conclusion, cellobiose/ipratropium bromide and lactose/ipratropium bromide blends were prepared and sized. The cellobiose blend has a higher mean particle size than does the lactose blend. The difference in the mean particle size between the two tested blends may suggest a slightly greater adhesion strength between cellobiose and ipratropium bromide than between lactose and ipratropium bromide, or may merely be a consequence of the different particle size distribution of the two materials. The particle size distribution of the blends inhaled into the Aerosizer by the Aerobreather also suggests similar performance of the two blends. The small difference in mean particle size of the inhaled particles may reflect difference in adhesion strength, particle size distribution or size selection of the retained powders but do not suggest markedly different performance. The cellobiose blend was found to be retained in capsules to a greater degree than the lactose blend. This result may reflect a slightly greater adhesion strength between cellobiose and ipratropium bromide than between lactose and ipratropium bromide, or again may be a consequence of the difference in the particle size distribution of the two materials.

Accordingly, the data collected suggests that the performance of cellobiose/ipratropium bromide and Pharmatose 200M/ipratropium bromide blends is similar under low humidity (<60% RH) conditions. The usefulness of cellobiose as a powder carrier was also evaluated by comparing the sintering rates of ground cellobiose, sifted cellobiose (passed through a 200 M U.S. standard mesh sieve, but caught on a 450 M sieve) and 200 M lactose (Pharmatose 200 M).

Two experiments were carried out, one at about 85% relative humidity and another at about 95% relative humidity. The experiments ran over several days, but the largest increment occurs fairly early. Both experiments were carried out at room temperature (about 23° C.). The results are shown in FIG. 1 and FIG. 2.

FIG. 1 is a graph of the relative sintering rates of sifted cellobiose, ground cellobiose and lactose, under conditions of approximately 85% relative humidity. The difference is number fraction, Δf, of particles given size is plotted versus particle diameter. Δf reflects the difference in number fraction after about one (1) day of exposure from that before exposure. Sintering of cellobiose is slower.

Figure 2:
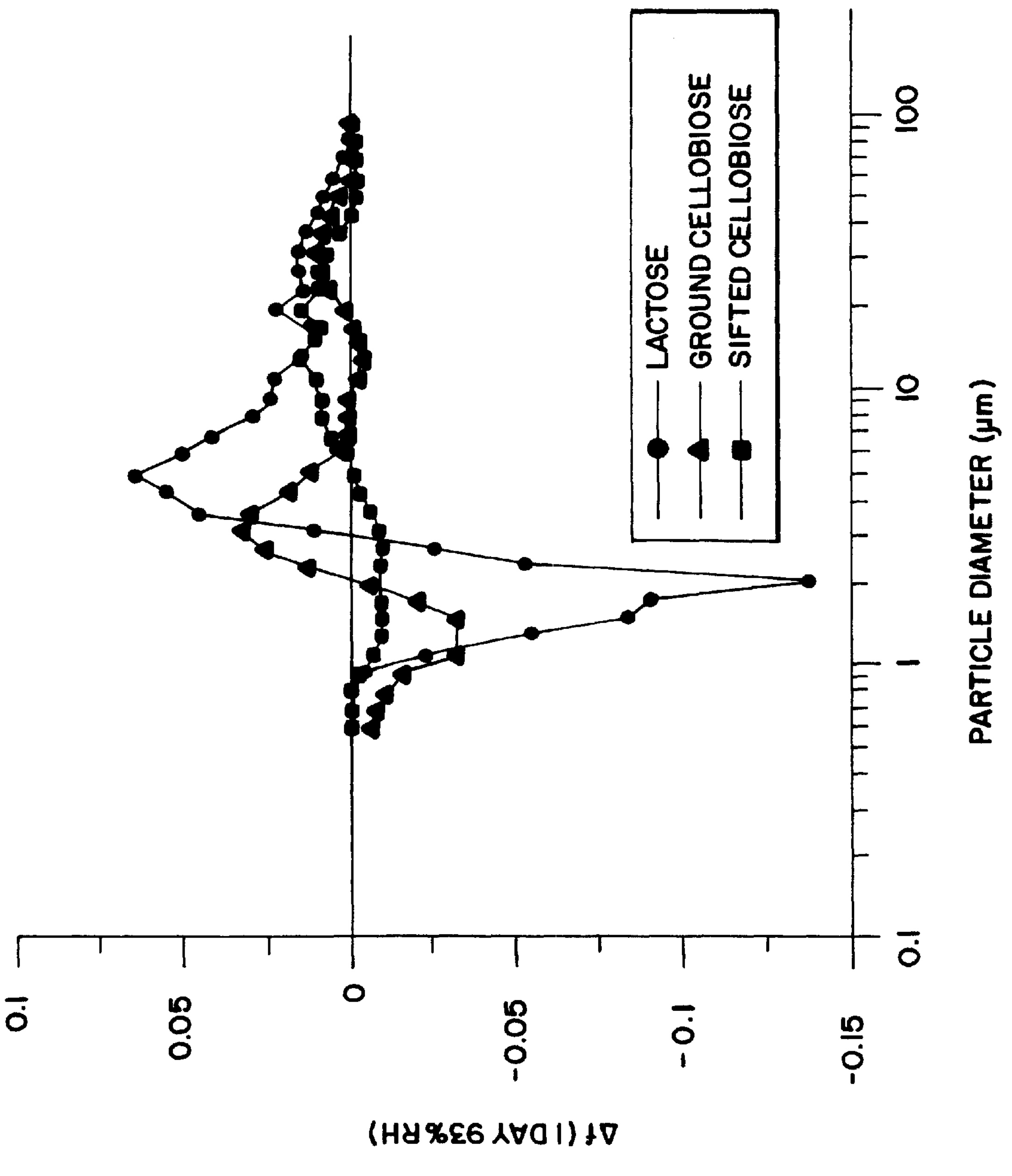
FIG. 2 is a graph of the relative sintering rates of sifted cellobiose, ground cellobiose and lactose under conditions of 93% relative humidity.

FIG. 2 is a graph of the relative sintering rates of sifted cellobiose, ground cellobiose and lactose under conditions of approximately 93% relative humidity. The difference in number fraction, Δf, of particles of given size is plotted versus particle diameter. Δf reflects the difference in number fraction after about one (1) day of exposure from that before exposure. Sintering of cellobiose is slower.

Since cellobiose is resistant to sintering, it appears that dry powder pharmaceutical formulations for use in capsules and for inhalation formulated with cellobiose as the carrier offer superior stability under humid conditions.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. An insufflation for the administration of a drug into a body cavity which consists of about 0.1% to about 3% by weight of a powder of ipratropium bromide, albuterol sulfate or tiotropium bromide together with a carrier, where the carrier is a finely divided powder selected from the group consisting of myoinositol, cellobiose or a mixture thereof.

2. The insufflation as recited in claim 1 wherein the carrier is cellobiose.

3. The insufflation as recited in claim 2 wherein the cellobiose is greater than about 1 μm and less than about 5 μm in diameter.

4. An insufflation for the administration of a drug into a body cavity which consists of about 0.1% to about 3% by weight of ipratropium bromide together with a carrier, where the carrier is finely divided cellobiose in powder form.

5. The insufflation as recited in claim 4 wherein the cellobiose is greater than about 1 μm and less than about 5μm in diameter.

6. An insufflation for the administration of a drug into a body cavity which consists of about 0.1% to about 3% by weight of tiotropium bromide together with a carrier, where the carrier is finely divided cellobiose in powder form.

7. The insufflation as recited in claim 6 wherein the cellobiose is greater than about 1 μm and less than about 5 μm in diameter.

* * * * *